(12) United States Patent
Almsick et al.

(10) Patent No.: US 8,188,002 B2
(45) Date of Patent: May 29, 2012

(54) 3-AMINO-2-NITRO-SUBSTITUTED BENZOYL DERIVATIVES AND USE THEREOF AS HERBICIDES

(75) Inventors: Andreas Almsick, Karben (DE); Jan Dittgen, Ghent (BE); Christopher Hugh Rosinger, Hofheim (DE); Isolde Häuser-Hahn, Leverkusen (DE); Dieter Feucht, Eschborn (DE)

(73) Assignee: Bayer Cropscience AG, Monheim (DE)

( * ) Notice: Subject to any disclaimer, the term of this patent is extended or adjusted under 35 U.S.C. 154(b) by 51 days.

(21) Appl. No.: 12/887,702

(22) Filed: Sep. 22, 2010

(65) Prior Publication Data

US 2011/0098179 A1  Apr. 28, 2011

Related U.S. Application Data

(60) Provisional application No. 61/246,305, filed on Sep. 28, 2009.

(30) Foreign Application Priority Data

Sep. 25, 2009 (EP) .................... 09012170

(51) Int. Cl.
*A01N 25/32* (2006.01)
*A01N 33/20* (2006.01)
*A01N 33/22* (2006.01)
*C07C 211/52* (2006.01)
*A01P 21/00* (2006.01)
*A01P 13/00* (2006.01)

(52) U.S. Cl. ........ 504/103; 504/148; 504/347; 564/440; 564/441

(58) Field of Classification Search ........ None
See application file for complete search history.

(56) References Cited

U.S. PATENT DOCUMENTS

| 4,780,127 A | 10/1988 | Michaely et al. |
| 5,006,158 A | 4/1991 | Carter et al. |
| 5,801,120 A | 9/1998 | Lee et al. |
| 6,211,216 B1 | 4/2001 | Willms et al. |

FOREIGN PATENT DOCUMENTS

| DE | 199 35 218 | 2/2001 |
| EP | 0186118 | 7/1986 |
| EP | 0338992 | 10/1989 |
| EP | 1 188 376 | 3/2002 |
| WO | 2005 123667 | 12/2005 |

OTHER PUBLICATIONS

International Search Report Based on PCT/EP2010/005740 Dated Oct. 20, 2010.
Barta et al.; "Benzoylcyclohexanedione Herbicides Are Strong Inhibitors of Purified P-hydroxyphenylpyruvic Acid Dioxygenase of Maize" Pesticide Science; BD. 45; NR. 3; Nov. 1, 1995; pp. 286-287.

*Primary Examiner* — Kamal Saeed
(74) *Attorney, Agent, or Firm* — Baker Donelson Bearman Caldwell & Berkowitz, PC

(57) ABSTRACT

A description is given of 3-amino-2-nitro-substituted benzoyl derivatives of the formula (I) as herbicides.

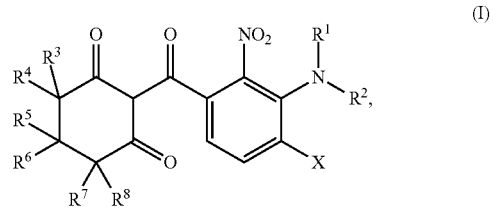

In this formula (I), X, $R^1$, $R^2$, $R^3$, $R^4$, $R^5$, $R^6$, $R^7$ and $R^8$ are radicals such as hydrogen, organic radicals such as alkyl, and other radicals such as halogen.

10 Claims, No Drawings

> # 3-AMINO-2-NITRO-SUBSTITUTED BENZOYL DERIVATIVES AND USE THEREOF AS HERBICIDES

CROSS REFERENCE TO RELATED APPLICATIONS

This application claims priority to European Application 09012170.8 filed Sep. 25, 2009 and U.S. Application 61/246,305 filed Sep. 28, 2009. The entire contents of which are hereby incorporated by reference in their entireties.

BACKGROUND OF THE INVENTION

1. Field of the Invention

The invention relates to the technical field of herbicides, in particular that of herbicides for the selective control of broad-leaved weeds and weed grasses in crops of useful plants.

2. Description of Related Art

From various publications it is already known that certain 2-nitro-substituted benzoyl derivatives possess herbicidal properties. For instance, U.S. Pat. No. 4,780,127, EP 186 118 A1 and EP 338 992 A1 describe 2-nitro-substituted benzoyl derivatives which are substituted on the phenyl ring by further radicals.

The herbicidal activity of the compounds known from these publications, however, is frequently inadequate. It is therefore an object of the present invention to provide further herbicidally active compounds having properties which—relative to those of the compounds disclosed in the state of the art—are improved.

SUMMARY

It has now been found that 3-amino-2-nitro-substituted benzoyl derivatives are especially suitable as herbicides.

The present invention provides 3-amino-2-nitro-substituted benzoyl derivatives of the formula (I) or salts thereof (I)

[Chemical structure showing cyclohexanedione ring with R³, R⁴, R⁵, R⁶, R⁷, R⁸ substituents, connected via a carbonyl to a benzene ring bearing NO₂, NR¹R², and X substituents]

in which

X is halogen, ethylsulfonyl, methylsulfonyl, 1,2,4-triazol-1-yl or 1,2,4-triazol-4-yl, R1 and R2 are independently of one another each hydrogen, (C1-C6)-alkyl, (C2-C6)-alkenyl, (C2-C6)-alkynyl, halo-(C1-C6)-alkyl, halo-(C1-C6)-alkenyl, halo-(C1-C6)-alkynyl, (C3-C6)-cycloalkyl-(C1-C6)-alkyl, (C3-C6)-cycloalkenyl-(C1-C6)-alkyl, (C1-C6)-alkoxy-(C1-C6)-alkyl, R4 and R7 independently of one another are each hydrogen or methyl, $R^3$ and $R^8$ independently of one another are each hydrogen or methyl, or $R^3$ and $R^8$ together form the group $CH_2CH_2$ or $CH=CH$, $R^5$ and $R^6$ independently of one another are each hydrogen or methyl, or $R^5$ and $R^6$, together with the carbon atom to which they are attached, form the group $C=O$.

In formula (I) and all the formulae below, alkyl radicals having more than two carbon atoms can be straight-chain or branched. Alkyl radicals are, for example, methyl, ethyl, n- or isopropyl, n-, iso-, t- or 2-butyl, pentyls, hexyls, such as n-hexyl, isohexyl and 1,3-dimethylbutyl. Halogen represents fluorine, chlorine, bromine or iodine.

Where a group is substituted by a plurality of radicals, this means that this group is substituted by one or more identical or different representatives of the radicals mentioned.

Depending on the nature and the attachment of the substituents, the compounds of the formula (I) may be present as stereoisomers. If, for example, one or more asymmetric carbon atoms are present, there may be enantiomers and diastereomers. Stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. The invention also relates to all stereoisomers and mixtures thereof embraced by the general formula (I) but not specifically defined.

DETAILED DESCRIPTION OF A PREFERRED EMBODIMENT

Preferred compounds of the general formula (I) are those in which

X is chlorine, bromine, fluorine or methylsulfonyl, $R^1$ and $R^2$ are independently of one another each hydrogen, $(C_1-C_6)$-alkyl, halo-$(C_1-C_6)$-alkyl, halo-$(C_1-C_6)$-alkenyl, $(C_3-C_6)$-cycloalkyl-$(C_1-C_6)$-alkyl or $(C_1-C_6)$-alkoxy-$(C_1-C_6)$-alkyl, $R^4$ and $R^7$ are independently of one another each hydrogen or methyl, $R^3$ and $R^8$ are independently of one another each hydrogen or methyl, or $R^3$ and $R^8$ together form the group $CH_2CH_2$, $R^5$ and $R^6$ are independently of one another each hydrogen or methyl, or $R^5$ and $R^6$, together with the carbon atom to which they are attached, form the group $C=O$.

Particularly preferred compounds of the formula (I) are those in which

X is chlorine or bromine,

R1 is hydrogen or methyl,

R2 is hydrogen, (C1-C4)-alkyl, halo-(C1-C4)-alkyl, (C3-C6)-cycloalkyl-(C1-C4)-alkyl or (C1-C4)-alkoxy-(C1-C4)-alkyl, R4 and R7 are independently of one another each hydrogen or methyl, R3 and R8 are independently of one another each hydrogen or methyl, or R3 and R8 together form the group CH2CH2, R5 and R6 are independently of one another each hydrogen or methyl, or R5 and R6, together with the carbon atom to which they are attached, form the group C=O.

The compounds of the formula (I) according to the invention may occur in different tautomeric structures, depending on external conditions, such as solvent and pH:

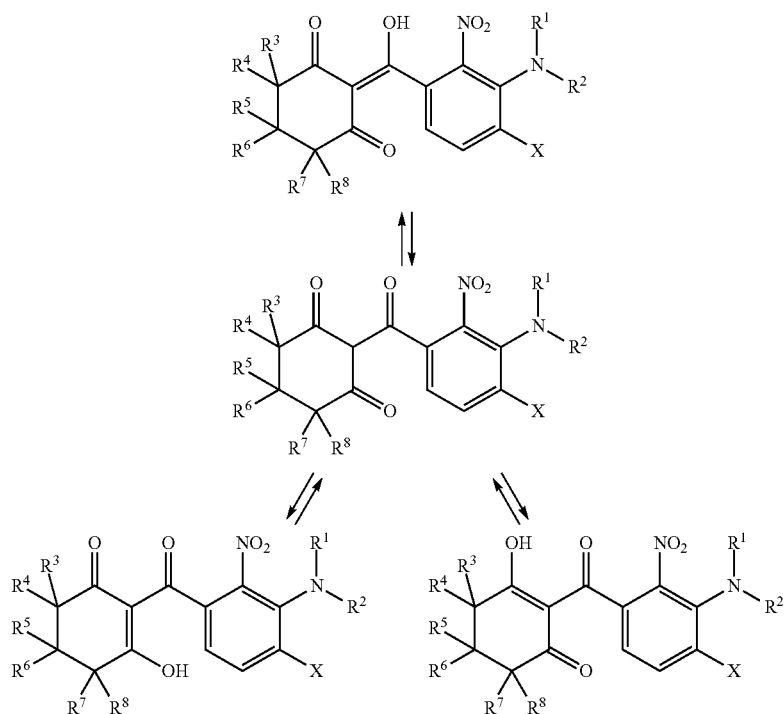

In all of the formulae given below, the substituents and symbols, unless defined otherwise, have the same definition as described under formula (I).

Depending on the nature of the substituents, the compounds of the formula (I) comprise an acidic proton which can be removed by reaction with a base. Examples of suitable bases include hydrides, hydroxides and carbonates of lithium, sodium, potassium, magnesium and calcium, and also ammonia and organic amines such as triethylamine and pyridine. Salts may also be formed by addition of organic acids, such as formic or acetic acid, and of inorganic acids, such as phosphoric, hydrochloric or sulfuric acid. Such salts are likewise provided by the invention.

Compounds of the formula (I) according to the invention are obtained, for example, by base-catalyzed reaction of 1,3-diketones of the formula (II) with benzoic acid derivatives of the formula (III), in which L is halogen, hydroxyl or alkoxy, and subsequent cyanide-induced rearrangement. If L is hydroxyl, it is preferred to operate in the presence of a water remover, such as dicyclocarbodiimide. Examples of cyanide sources for the rearrangement of the enol esters (III) to the compounds (I) according to the invention include potassium cyanide, acetone cyanohydrin and trimethylsilyl cyanide, preferably in an amount of 1 to 50 mole percent. Examples for the cyanide-catalyzed rearrangement of enol esters are found in WO 00/21924 or U.S. Pat. No. 6,297,196, for example.

The 1,3-diketones of the formula (II) used as starting material are known, are available commercially or can be prepared by processes that are known per se, of the kind described, for example, in EP-A 71707, EP-A 142741, EP-A 243313, U.S. Pat. No. 4,249,937, WO 92/13821, WO 2002/006197 and WO 2005/123667.

Scheme 1

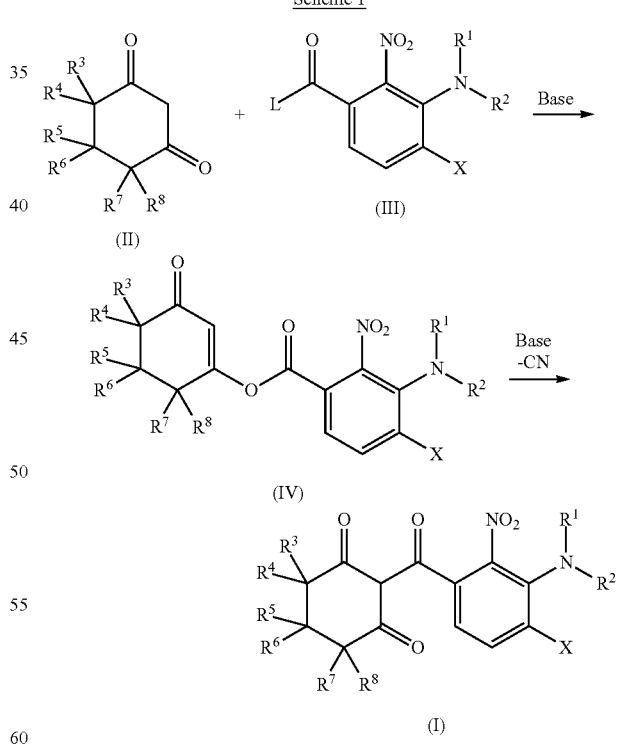

The benzoic acid derivatives (III) can be prepared, for example, in accordance with schemes 2 to 4, by means of reactions that are known in principle to a person skilled in the art, from the compounds (V). Accordingly it is possible, as shown in scheme 2, for example, to convert 3-amino-benzoic acids (V) in which X is halogen in a conventional way, through reaction, for example, with acetic anhydride and a catalytic amount of concentrated sulfuric acid, into the corresponding acetamides (VI). The conversion to the corresponding esters (VII) in which L is alkoxy is accomplished with the customary, known esterification methods, but advantageously by reaction of dimethyl sulfate or diethyl sulfate in the presence of potassium carbonate in a suitable solvent such as N,N-dimethylformamide. The subsequent nitration leads to compounds (VIII), which are reacted with a sulfuric acid/alcohol mixture to give the corresponding 3-amino-2(6)-nitro-benzoic esters (IX).

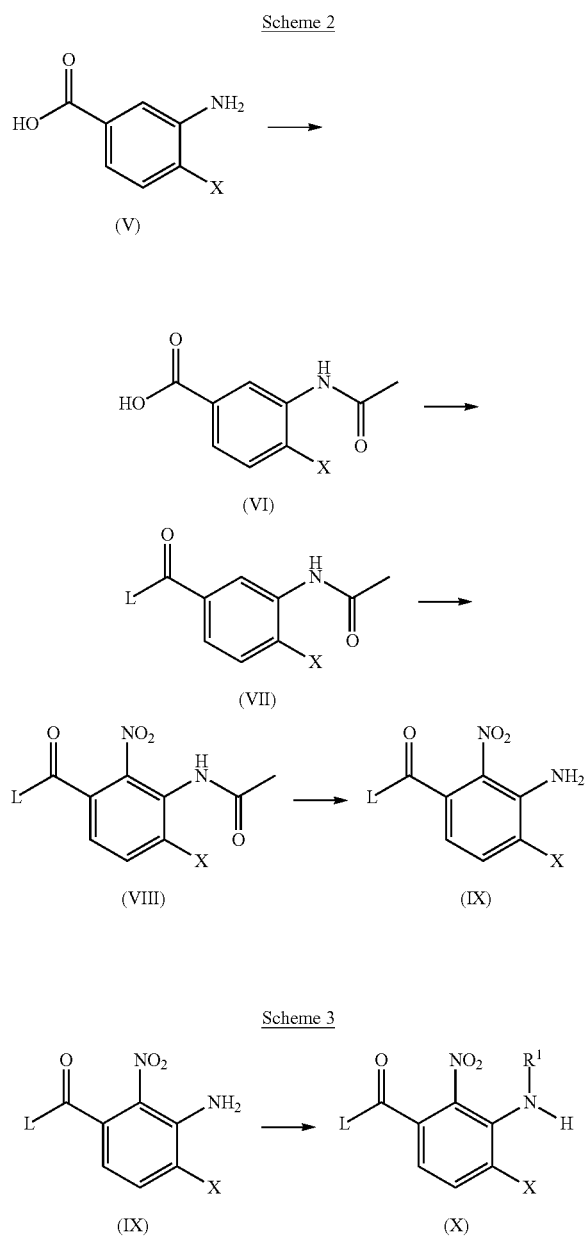

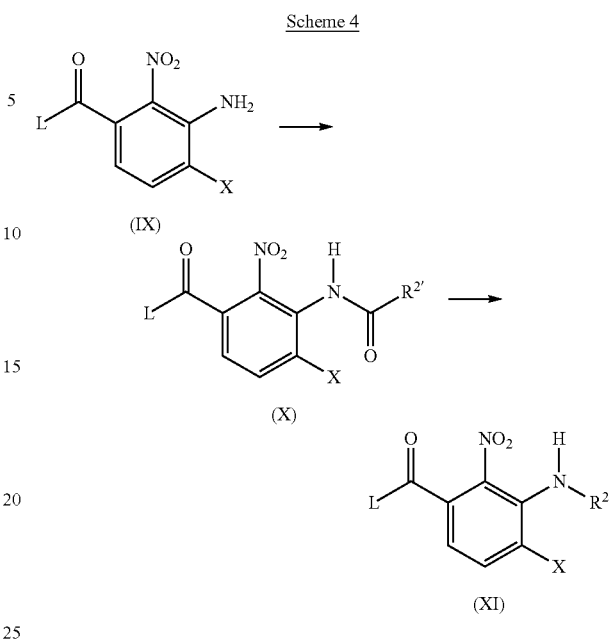

According to scheme 3, a 3-amino-2-nitro-benzoic ester of the formula (IX) is reacted with a suitable methylating agent such as methyl iodide in the presence of a suitable strong base such as sodium hydride in a suitable solvent such as DMF to give the monomethylamine derivative (X).

According to scheme 4, 3-amino-2-nitro-benzoic esters of the formula (IX) are converted by conventional methods with suitable acylating agents, such as anhydrides or acid chlorides, under appropriate conditions, into the corresponding amides (X). $R^{2'}$ therein is the radical $R^2$ minus one $CH_2$ unit. The compounds (XI) can then be reacted by the method specified in scheme 3, by introduction of the radical $R^1$, to give the compounds (III).

Collections of compounds of the formula (I) and/or salts thereof which can be synthesized by the aforementioned reactions can also be prepared in a parallel manner, it being possible for this to take place in a manual, partly automated or completely automated manner. In this connection, it is, for example, possible to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, it is possible to use a series of commercially available instruments, for example Calypso reaction blocks from Barnstead International, Dubuque, Iowa 52004-0797, USA or reaction stations from Radleys, Shirehill, Saffron Walden, Essex, CB11 3AZ, England or MultiPROBE automated workstations from Perkin Elmer, Waltham, Mass. 02451, USA. For the parallel purification of compounds of the formula (I) and salts thereof or of intermediates produced during the preparation, there are available, inter alia, chromatography apparatuses, for example from ISCO, Inc., 4700 Superior Street, Lincoln, Nebr. 68504, USA.

The apparatuses listed lead to a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Caliper, Hopkinton, Mass. 01748, USA.

The implementation of single or several synthesis steps can be supported through the use of polymer-supported reagents/ scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described here, the preparation of compounds of the formula (I) and salts thereof can take place completely or partially by solid-phase supported methods. For this purpose, individual intermediates or all intermediates in the synthesis or a synthesis adapted for the corresponding procedure are bonded to a synthesis resin. Solid-phase supported synthesis methods are sufficiently described in the specialist literature, e.g. Barry A. Bunin in "The Combinatorial Index", Verlag Academic Press, 1998 and Combinatorial Chemistry—Synthesis, Analysis, Screening (editor Günther Jung), Verlag Wiley, 1999. The use of solid-phase supported synthesis methods permits a series of protocols known in the literature, which again can be carried out manually or in an automated manner. The reactions can be carried out, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editors C. O. Kappe and A. Stadler), Verlag Wiley, 2005.

The preparation according to the process described here produces compounds of the formula (I) and their salts in the form of substance collections which are called libraries. The present invention also provides libraries which comprise at least two compounds of the formula (I) and their salts.

The compounds of the formula (I) according to the invention (and/or their salts), hereinbelow also referred to together as "compounds according to the invention", have excellent herbicidal efficacy against a broad spectrum of economically important monocotyledonous and dicotyledonous annual harmful plants. The active compounds act efficiently even on perennial weeds which produce shoots from rhizomes, root stocks and other perennial organs and which are difficult to control.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous broad-leaved weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum,* are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant-growth-regulatory properties, the active compounds can also be employed for controlling harmful plants in crops of genetically modified plants or plants modified by conventional mutagenesis. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

It is preferred, with respect to transgenic crops, to use the compounds according to the invention in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

It is preferred to use the compounds according to the invention or their salts in economically important transgenic crops of useful plants and ornamentals, for example of cereals such as wheat, barley, rye, oats, millet, rice, cassava and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), glufosinate (cf., for example, EP-A-0242236, EP-A-242246) or glyphosate (WO 92/00377) or the sulfonylureas (EP-A-0257993, U.S. Pat. No. 5,013,659), transgenic crop plants, for example cotton, with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example, of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, nucleic acid molecules which allow mutagenesis or sequence changes by recombination of DNA sequences can be introduced into plasmids. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product. To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds according to the invention in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell, Stuttgart 1976; Winnacker-Küchler, "Chemische Technologie", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyrdiethyl, cyprosulfamide, isoxadifen-ethyl, cloquintocetmexyl and dichlormid.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are ground finely, for example in customary apparatus such as hammer mills, blower mills and air-jet mills, and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Formulations in the form of dusts comprise from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. Here, by way of example, one and in some cases a plurality of use forms are mentioned:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-natrium, bispyribac, bispyribac-natrium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-natrium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-natrium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron-methyl, ephephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]-phenyl]-ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-natrium, ioxynil, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleinsäurehydrazid, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropen, methylisothiocyanat, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat-dichlorid, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-natrium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and also the following compounds

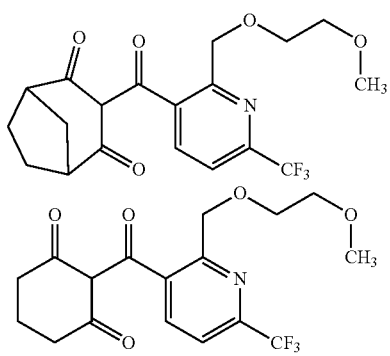

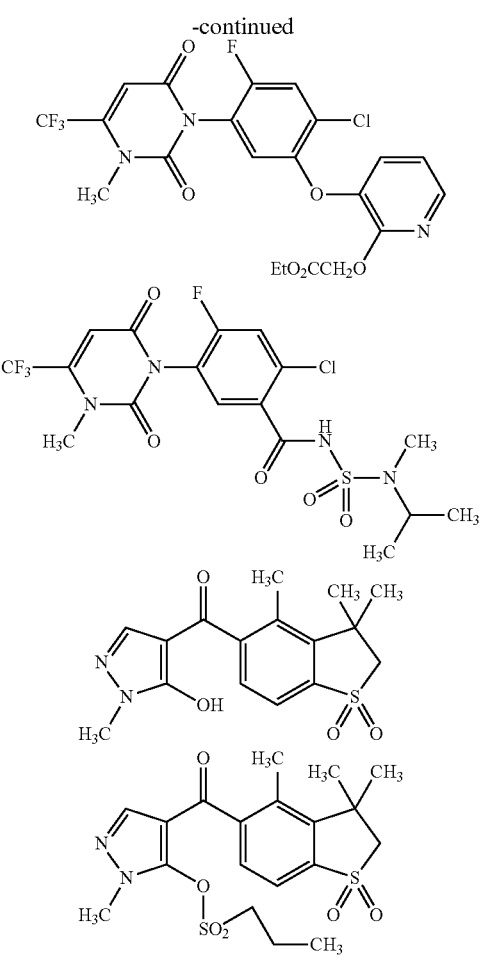

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application.

The required application rate of the compounds of the formula (I) varies according to the external conditions such as, inter alia, temperature, humidity and the type of herbicide used. It may vary within wide limits, for example between 0.001 and 1.0 kg/ha or more of active substance; however, preferably it is between 0.005 and 750 g/ha.

The examples which follow illustrate the invention.

A. Chemical Examples

Preparation of 2-[4-chloro-3-(methylamino)-2-nitrobenzoyl]-5-methylcyclohexane-1,3-dione, (Table Example No. 2-2)

Step 1: Synthesis of 3-acetamido-4-chlorobenzoic acid

Tetrahydrofuran (THF) room temperature (RT), NaHCO$_3$ solution 101.9 g (582 mmol) of 3-amino-4-chlorobenzoic acid were suspended in 700 ml of acetic acid and then admixed with 64.8 ml (687 mmol) of acetic anhydride. The mixture was heated under reflux for 15 h and, after cooling, was added to 1.5 l of ice-water. The precipitated crystals were isolated by filtration with suction, washed with water, and dried in a vacuum cabinet at 70° C. for 17 h.

$^1$H NMR (DMSO): δ 2.12 (s, 3H), 7.6 (d, 1H), 7.7 (dd, 1H), 8.31 (s, 1H), 9.63 (s, 1H), 13.18 (s, 1H)

Yield: 120.09 g (562 mmol), 97%, pale beige crystals

Step 2: Synthesis of ethyl 3-acetamido-4-chlorobenzoate 120 g (562 mmol) of 3-acetamido-4-chlorobenzoic acid were dissolved in 77 ml of DMF and stirred with 93.16 g (674 mmol) of potassium carbonate at 60° C. for 30 min. The mixture was then cooled, admixed with 91 g (590 mmol) of diethyl sulfate, and left with stirring at RT for 7 h. The batch was concentrated, the residue was stirred with 2 l of water, and the precipitated crystals were isolated by filtration with suction. They were washed with water and dried in a vacuum cabinet at 70° C. for 3 h.

$^1$H NMR (CDCl3): δ 1.4 (t, 3H), 2.26 (s, 3H), 4.38 (q, 2H), 7.44 (d, 1H), 7.6 (s, br, 1H), 7.75 (dd, 1H), 8.95 (s, br, 1H)

Yield: 133.40 g (552 mmol), 97%, pale beige crystals

Step 3: Synthesis of ethyl 3-acetamido-4-chloro-2-nitrobenzoate 133.4 g (552 mmol) of ethyl 3-acetamido-4-chlorobenzoate were introduced at −10° C. and were admixed at between −10 to 0° C., with cooling, with 207 ml of 100% strength nitric acid. The batch was stirred at −5° C. for 2 h. It was then added to 2.1 l of ice-water and the precipitated crystals were isolated by filtration with suction, washed with water, and dried in a vacuum cabinet at 60° C.

Yield: 138.63 g of light brown crystals, consisting of a mixture of 40.2% of ethyl 3-acetamido-4-chloro-2-nitrobenzoate, 35.9% of ethyl 5-acetamido-4-chloro-2-nitro-benzoate and 13.6% of starting material

Step 4: Synthesis of ethyl 3-amino-4-chloro-2-nitrobenzoate 138.63 g of the mixture from step 3 were dissolved in 1.4 l of ethanol and 60 ml of concentrated sulfuric acid and the solution was boiled at reflux for 25 h. Then 1.3 l of ethanol were removed on a rotary evaporator and the residue was admixed with 1 l of ice-water, rendered basic using saturated NaHCO$_3$ solution, and then extracted with three times 500 ml of dichloromethane. The combined organic phases were dried over MgSO$_4$, filtered with suction over silica gel, and concentrated. The product was then subjected to chromatographic separation (silica gel, heptane/ethyl acetate 9:1).

$^1$H NMR (CDCl3): δ 1.35 (t, 3H), 4.35 (q, 2H), 6 (s, br, 2H), 6.88 (d, 1H), 7.5 (d, 1H)

Yield: 53.0 g (217 mmol) of orange oil

Step 5: Synthesis of ethyl 4-chloro-3-(methylamino)-2-nitrobenzoate 3.18 g (13.0 mmol) of ethyl 3-amino-4-chloro-2-nitrobenzoate were introduced in DMF and admixed under a nitrogen atmosphere with 0.624 g (15.6 mmol) of sodium hydride. The mixture was left with stirring for 30 minutes and then 2.21 g (15.6 mmol) of methyl iodide were added. After a further 2.5 h of stirring at room temperature the mixture was concentrated and the residue was extracted with ethyl acetate, washed with water, and then dried over MgSO$_4$. The product was then subjected to chromatographic separation (silica gel, heptane/ethyl acetate 9:1).

$^1$H NMR (CDCl3): δ 1.33 (t, 3H), 2.91 (d, 1H), 4.33 (q, 2H), 4.8 (s, br, 1H), 7.2 (d, 1H), 7.42 (d, 1H)

Yield: 3.01 g (11.6 mmol) 86%, orange oil

Step 6: Synthesis of 4-chloro-3-(methylamino)-2-nitrobenzoic acid 3.01 g (11.6 mmol) of ethyl 4-chloro-3-(methylamino)-2-nitrobenzoate were dissolved in 35 ml of tetrahydrofuran and 22 ml of water and this solution was admixed with 0.5 g (20.9 mmol) of lithium hydroxide. It was left with stirring for 8 h and then concentrated. The residue was taken up in water and washed with methylene chloride, and the aqueous phase was then adjusted to a pH of 1 using a KHSO$_4$ solution. The precipitate was isolated by filtration with suction, washed with water, and dried under reduced pressure at 70° C.

$^1$H NMR (CDCl3): δ 2.91 (s, 3H), 7.32 (d, 1H), 7.45 (d, 1H)

Yield: 2.30 g (10.0 mmol), 86%, orange crystals

Step 7: Synthesis of 5-methyl-3-oxocyclohex-1-en-1-yl 3-amino-4-chloro-2-nitrobenzoate 250 mg (1.1 mmol) of 4-chloro-3-(methylamino)-2-nitrobenzoic acid, 410.3 mg (3.3 mmol) of 5-methylcyclohexane-1,3-dione, 275.7 mg (1.4 mmol) of N-(3-dimethylaminopropyl)-N'-ethylcarbodiimide hydrochloride and 13.5 mg (0.1 mmol) of 4-(dimethylamino)pyridine were dissolved in 6 ml of methylene dichloride and stirred at RT for 8 h. This was followed by washing with water and saturated NaHCO$_3$ solution, after which the organic phase was dried over MgSO$_4$ and then the whole was filtered through a small glass frit filled with 1 cm of silica gel, with suction, and the filter product was washed with heptane/ethyl acetate 1:2. The filtrate was concentrated.

$^1$H NMR (CDCl3): δ 1.15 (d, 3H), 2.15 (m, 1H), 2.3-2.6 (m, 4H), 2.96 (d, 3H), 5.08 (d, br, 1H), 6.0 (d, 1H), 7.2 (d, 1H), 7.49 (d, 1H)

Yield: 296.5 mg (0.88 mmol), 81%

Step 8: Synthesis of 2-[4-chloro-3-(methylamino)-2-nitrobenzoyl]-5-methylcyclo-hexane-1,3-dione 290 mg (0.86 mmol) of 5-methyl-3-oxocyclohex-1-en-1-yl-3-amino-4-chloro-2-nitro-benzoate, 164.6 mg (1.6 mmol) of triethylamine, 23.4 mg (0.36 mmol) of potassium cyanide and 7.3 mg (0.086 mmol) of acetone cyanohydrin were stirred in 15 ml of acetonitrile at RT for 24 h. The mixture was then concentrated and the residue was admixed with 30 ml of saturated KHSO$_4$ solution and extracted with methylene chloride. The combined organic phases were dried over MgSO$_4$ and isolated by filtration through a small glass frit, filled with 5 cm of silica gel, followed by washing with ethyl acetate. The filtrate was concentrated.

¹H NMR (CDCl3): δ 1.1 (d, 3H), 2.08-2.18 (m, 1H), 2.22-2.35 (m, 1H), 2.4-2.51 (m, 1H), 2.75-2.82 (m, 1H), 3.06 (d, 3H), 6.45 (d, 1H), 6.52 (s, br, 1H), 7.45 (d, 1H), 16.45 (s, 1H)

Yield: 98 mg (0.29 mmol), 34%

Preparation of 2-{4-bromo-3-[(2,2-dimethylpropyl)amino]-2-nitrobenzoyl}cyclohexane-1,3-dione,
(Table Example No. 1-23)

Step 1: Synthesis of methyl 4-bromo-3-[(2,2-dimethylpropanoyl)amino]-2-nitro-benzoate 3.0 g (10.9 mmol) of methyl 3-amino-4-bromo-2-nitrobenzoate were mixed with 5 ml of pivalic anhydride and admixed under reflux with 0.06 ml of concentrated sulfuric acid. The mixture was left boiling for an hour and then cooled. The batch was diluted with water and the precipitated solid was isolated by filtration with suction. It was then washed with water and heptane and gel-filtered over silica gel with methylene chloride.

¹H NMR (CDCl₃): δ 1.31 (s, 9H), 3.9 (s, 3H), 7.3 (s, br, 1H), 7.75 (d, 1H), 7.85 (d, 1H)

Yield: 3.81 g (10.6 mmol), 97%, yellow crystals

Step 2: Synthesis of methyl 4-bromo-3-[(2,2-dimethylpropyl)amino]-2-nitrobenzoate 3.76 g (10.47 mmol) of methyl 4-bromo-3-[(2,2-dimethylpropanoyl)amino]-2-nitro-benzoate were suspended in toluene and admixed with 6 ml (11.26 mmol) of borane-dimethyl sulfide (2M in toluene). The mixture was left with stirring under reflux for 15 h and then cooled. Thereafter, 50 ml of saturated NaHCO₃ solution were added, stirring was carried out again at RT for 30 min, and then the organic phase was separated off, dried over MgSO₄ and concentrated. The product was then subjected to chromatographic separation (silica gel, heptane/ethyl acetate 4:1).

¹H NMR (CDCl₃): δ 0.98 (s, 9H), 2.85 (d, 2H), 3.89 (s, 3H), 4.58 (s, br, 1H), 7.15 (d, 1H), 7.62 (d, 1H)

Yield: 0.89 g (2.58 mmol), 25%, yellow crystals

Step 3: Synthesis of 4-bromo-3-[(2,2-dimethylpropyl)amino]-2-nitrobenzoic acid 0.88 g (2.55 mmol) of methyl 4-bromo-3-[(2,2-dimethylpropyl)amino]-2-nitrobenzoate was dissolved in 10 ml of tetrahydrofuran and 10 ml of water and admixed with 0.064 g (2.67 mmol) of lithium hydroxide. The mixture was left with stirring for 15 h and then concentrated. The residue was taken up in water and washed with methylene chloride and the aqueous phase was adjusted to a pH of 1 using a KHSO₄ solution. The precipitate was isolated by filtration with suction, washed with water and dried under reduced pressure at 70° C.

¹H NMR (DMSO): δ 2.50 (s, 9H), 2.75 (d, 2H), 4.68 (t, br, 1H), 7.23 (d, 1H), 7.88 (d, 1H), 13.85 (s, br, 1H)

Yield: 0.812 g (2.45 mmol), 96%, yellow crystals

Step 4: Synthesis of 3-oxocyclohex-1-en-1-yl 4-bromo-3-[(2,2-dimethylpropyl)amino]-2-nitrobenzoate 190 mg (0.574 mmol) of 4-bromo-3-[(2,2-dimethylpropyl)amino]-2-nitrobenzoic acid, 198 mg (1.713 mmol) of cyclohexane-1,3-dione, 145 mg (0.741 mmol) of N-(3-dimethylaminopropyl)-N'-ethylcarbodiimide hydrochloride and 7 mg (0.057 mmol) of 4-(dimethylamino)pyridine were dissolved in 5 ml of methylene dichloride and stirred at RT for 24 h. The solution was then washed with water and saturated NaHCO₃ solution, the organic phase was dried over MgSO₄, and then the whole was filtered with suction through a glass frit, filled with 1 cm of silica gel, and the filter product was washed with heptane/ethyl acetate 1:2. The filtrate was concentrated.

¹H NMR (CDCl₃): δ 0.98 (s, 9H), 2.10 (m, 2H), 2.45 (m, 2H), 2.62 (m, 2H), 2.94 (d, 2H), 5.01 (t, br, 1H), 6.0 (s, 1H), 7.20 (d, 1H), 7.50 (d, 1H)

Yield: 68 mg (0.16 mmol), 28%, yellow oil

Step 5: Synthesis of 2-{4-bromo-3-[(2,2-dimethylpropyl)amino]-2-nitrobenzoyl}-cyclohexane-1,3-dione 68 mg (0.144 mmol) of 3-oxocyclohex-1-en-1-yl 4-bromo-3-[(2,2-dimethylpropyl)amino]-2-nitrobenzoate, 29 mg (0.287 mmol) of triethylamine, 4 mg (0.061 mmol) of potassium cyanide and 1 mg (0.015 mmol) of acetone cyanohydrin were stirred in 3 ml of acetonitrile at room temperature for 60 h. The mixture was then concentrated and the residue was admixed with 30 ml of saturated KHSO₄ solution and extracted with methylene chloride. The combined organic phases were dried over MgSO₄ and filtered through a small glass frit filled with 5 cm of silica gel, and the filter product was washed with heptane/ethyl acetate 1:2. The filtrate was concentrated.

¹H NMR (CDCl₃): δ 0.98 (s, 9H), 2.03 (m, 2H), 2.39 (m, 2H), 2.78 (m, 2H), 3.12 (d, 2H), 6.42 (d, 1H), 7.45 (d, 1H), 16.50 (s, 1H)

Yield: 56 mg (0.118 mmol), 82%, yellow oil

The examples listed in tables below were prepared in analogy to methods identified above or are obtainable in analogy to methods identified above. These compounds are in each case very particularly preferred.

The abbreviations used have the following meanings:
Et=ethyl Me=methyl Pr=propyl Bu=butyl

TABLE 1

Inventive compounds of the formula (I) in which $R^3$, $R^4$, $R^5$, $R^6$, $R^7$ and $R^8$ are each hydrogen

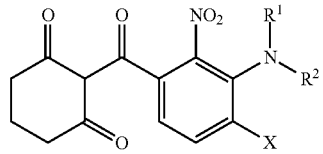

| No. | X | $R^1$ | $R^2$ | Physical data: ¹H NMR: δ [CDCl₃] |
|---|---|---|---|---|
| 1-1 | Cl | H | H | 2.02 (m, 2H), 2.38 (t, 2H), 2.78 (t, 2H), 6.38 (d, 1H), 6.65 (s, br, 2H), 7.51 (d, 1H), 16.45 (s, 1H) |

TABLE 1-continued

Inventive compounds of the formula (I) in which $R^3$, $R^4$, $R^5$, $R^6$, $R^7$ and $R^8$ are each hydrogen

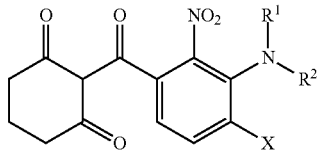

| No. | X | $R^1$ | $R^2$ | Physical data: $^1$H NMR: δ [CDCl$_3$] |
|---|---|---|---|---|
| 1-2 | Cl | H | Me | 2.03 (m, 2H), 2.4 (t, 2H), 2.78 (t, 2H), 3.08 (s, 3H), 6.43 (d, 1H), 6.52 (s, br, 1H), 7.45 (d, 1H), 16.48 (s, 1H) |
| 1-3 | Cl | Me | Me | 2.05 (m, 2H), 2.42 (t, 2H), 2.78 (t, 2H), 2.85 (s, 6H), 6.88 (d, 1H), 7.5 (d, 1H), 16.45 (s, 1H) |
| 1-4 | Cl | H | Et | 1.25 (t, 3H), 2.05 (m, 2H), 2.4 (t, 2H), 2.78 (t, 2H), 3.4 (q, 2H), 6.48 (d, 1H), 7.46 (d, 1H), 16.5 (s, 1H) |
| 1-5 | Cl | H | nPr | 0.95 (t, 3H), 1.65 (q, 2H), 2.02 (m, 2H), 2.40 (t, 2H), 2.75 (t, 2H), 3.32 (t, 2H), 6.45 (d, 1H), 7.45 (d, 1H), 16.5 (s, br, 1H) |
| 1-6 | Cl | H | nBu | 0.92 (t, 3H), 1.39 (m, 2H), 1.6 (m, 2H), 2.05 (m, 2H), 2.39 (m, 2H), 2.75 (m, 2H), 3.36 (t, 2H), 3.2 (t, 2H), 6.45 (d, 1H), 6.48 (s, br, 1H), 7.45 (d, 1H), 16.48 (s, 1H) |
| 1-7 | Cl | H | CH$_2$iPr | 0.95 (d, 6H), 1.85 (m, 1H), 2.02 (m, 2H), 2.4 (t, 2H), 2.76 (7, 2H), 3.19 (m, 2H), 6.45 (d, 2H), 7.45 (d, 2H), 16.48 (s, 1H) |
| 1-8 | Cl | H | CH$_2$cPr | 0.25 (m, 2H), 0.55 (m, 2H), 1.05 (m, 1H), 2.03 (m, 2H), 2.39 (m, 2H), 2.78 (m, 2H), 3.18 (d, 2H), 6.48 (d, 1H), 6.55 (s, br, 1H), 7.45 (d, 1H), 16.50 (s, 1H) |
| 1-9 | Cl | H | CH$_2$tBu | 0.98 (s, 9H), 2.03 (m, 2H), 2.39 (m, 2H), 2.78 (m, 2H), 3.12 (d, 2H), 6.45 (d, 1H), 7.45 (d, 1H), 16.50 (s, 1H) |
| 1-10 | Cl | H | CH$_2$CH$_2$iPr | 0.90 (d, 6H), 1.5 (m, 2H), 1.68 (m, 1H), 2.05 (m, 2H), 2.4 (m, 2H), 2.75 (m, 2H), 3.38 (m, 2H), 6.45 (s, br, 1H), 6.45 (d, 1H), 7.45 (d, 1H), 16.48 (s, 1H) |
| 1-11 | Cl | H | CH$_2$CH$_2$OMe | |
| 1-12 | Cl | H | CH$_2$CH$_2$OEt | |
| 1-13 | Cl | H | CH$_2$CH$_2$CH$_2$OMe | |
| 1-14 | Cl | H | CH$_2$CH$_2$CH$_2$OMe | |
| 1-15 | Br | H | H | 2.02 (m, 2H), 2.38 (t, 2H), 2.78 (t, 2H), 6.3 (d, 1H), 6.7 (s, br, 2H), 7.68 (d, 1H), 16.45 (s, br, 1H) |
| 1-16 | Br | H | Me | 2.02 (m, 2H), 2.4 (t, 2H), 2.78 (t, 2H), 2.98 (s, 3H), 6.4 (d, 1H), 7.62 (d, 1H), 16.48 (s, 1H) |
| 1-17 | Br | Me | Me | δ [MeOD] = 2.05 (m, 2H), 2.62 (m, 4H), 2.85 (s, 6H), 7.01 (d, 1H), 7.8 (d, 1H) |
| 1-18 | Br | H | Et | 1.28 (t, 3H), 2.02 (m, 2H), 2.4 (t, 2H), 2.75 (t, 2H), 3.28 (q, 2H), 5.8 (s, br, 1H), 6.42 (d, 1H), 7.65 (d, 1H), 16.48 (s, 1H) |
| 1-19 | Br | H | nPr | 0.98 (t, 3H), 1.62 (m, 2H), 2.02 (m, 2H), 2.4 (t, 2H), 2.75 (t, 2H), 3.18 (t, 2H), 6.42 (d, 1H), 7.65 (d, 1H), 16.5 (s, 1H) |
| 1-20 | Br | H | nBu | 0.92 (t, 3H), 1.39 (m, 2H), 1.6 (m, 2H), 2.05 (m, 2H), 2.41 (m, 2H), 2.78 (m, 2H), 3.12 (t, 2H), 3.2 (t, 2H), 6.42 (d, 1H), 7.65 (d, 1H), 16.5 (s, 1H) |
| 1-21 | Br | H | CH$_2$iPr | 0.95 (d, 6H), 1.85 (m, 1H), 2.02 (m, 2H), 2.4 (t, 2H), 2.76 (7, 2H), 3.02 (m, 2H), 5.98 (s, 1H), 6.4 (d, 2H), 7.62 (d, 2H), 16.48 (s, 1H) |
| 1-22 | Br | H | CH$_2$cPr | 0.25 (m, 2H), 0.55 (m, 2H), 1.05 (m, 1H), 2.03 (m, 2H), 2.39 (m, 2H), 2.78 (m, 2H), 3.18 (d, 2H), 6.48 (d, 1H), 7.45 (d, 1H), 16.50 (s, 1H) |
| 1-23 | Br | H | CH$_2$tBu | 0.98 (s, 9H), 2.03 (m, 2H), 2.39 (m, 2H), 2.78 (m, 2H), 3.12 (d, 2H), 6.42 (d, 1H), 7.45 (d, 1H), 16.50 (s, 1H) |
| 1-24 | Br | H | CH$_2$CH$_2$iPr | 0.90 (d, 6H), 1.5 (m, 2H), 1.7 (m, 1H), 2.05 (m, 2H), 2.4 (m, 2H), 2.78 (m, 2H), 3.22 (m, 2H), 5.88 (t, br, 1H), 6.42 (d, 1H), 7.65 (d, 1H), 16.48 (s, 1H) |
| 1-25 | Br | H | CH$_2$CH$_2$OMe | |
| 1-26 | Br | H | CH$_2$CH$_2$OEt | |
| 1-27 | Br | H | CH$_2$CH$_2$CH$_2$OMe | |
| 1-28 | Br | H | CH$_2$CH$_2$CH$_2$OMe | |
| 1-29 | F | H | H | δ [DMSO] = 1.9 (m, 2H), 2.38 (m, 2H), 2.65 (m, 2H), 6.38 (dd, 1H), 7.4 (dd, 1H), 16.25 (s, br, 1H) |

TABLE 1-continued

Inventive compounds of the formula (I) in which $R^3$, $R^4$, $R^5$, $R^6$, $R^7$ and $R^8$ are each hydrogen

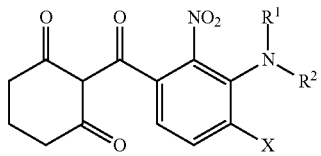

| No. | X | $R^1$ | $R^2$ | Physical data: $^1$H NMR: δ [CDCl$_3$] |
|---|---|---|---|---|
| 1-30 | F | H | Me | |
| 1-31 | F | Me | Me | δ [MeOD] = 2.05 (m, 2H), 2.62 (m, 4H), 3.12 (s, 6H), 6.92 (d, 2H), 7.88 (dd, 1H) |
| 1-32 | F | H | Et | |
| 1-33 | F | H | nPr | |
| 1-34 | F | H | nBu | |
| 1-35 | F | H | CH$_2$iPr | |
| 1-36 | F | H | CH$_2$cPr | |
| 1-37 | F | H | CH$_2$tBu | |
| 1-38 | F | H | CH$_2$CH$_2$iPr | |
| 1-39 | F | H | CH$_2$CH$_2$OMe | |
| 1-40 | F | H | CH$_2$CH$_2$OEt | |
| 1-41 | F | H | CH$_2$CH$_2$CH$_2$OMe | |
| 1-42 | F | H | CH$_2$CH$_2$CH$_2$OMe | |
| 1-43 | SO$_2$Me | H | H | 2.05 (m, 2H), 2.4 (t, 2H), 2.8 (t, 2H), 3.15 (s, 3H), 6.52 (d, 1H), 7.62 (s, br, 2H), 8.08 (d, 1H), 16.1 (s, br, 1H) |
| 1-44 | SO$_2$Me | H | Me | |
| 1-45 | SO$_2$Me | Me | Me | |
| 1-46 | SO$_2$Me | H | Et | |
| 1-47 | SO$_2$Me | H | nPr | |
| 1-48 | SO$_2$Me | H | nBu | |
| 1-49 | SO$_2$Me | H | CH$_2$iPr | |
| 1-50 | SO$_2$Me | H | CH$_2$cPr | |
| 1-51 | SO$_2$Me | H | CH$_2$tBu | |
| 1-52 | SO$_2$Me | H | CH$_2$CH$_2$iPr | |
| 1-53 | SO$_2$Me | H | CH$_2$CH$_2$OMe | |
| 1-54 | SO$_2$Me | H | CH$_2$CH$_2$OEt | |
| 1-55 | SO$_2$Me | H | CH$_2$CH$_2$CH$_2$OMe | |
| 1-56 | SO$_2$Me | H | CH$_2$CH$_2$CH$_2$OMe | |
| 1-57 | SO$_2$Et | H | H | |
| 1-58 | SO$_2$Et | H | Me | |
| 1-59 | SO$_2$Et | Me | Me | |
| 1-60 | SO$_2$Et | H | Et | |
| 1-61 | SO$_2$Et | H | nPr | |
| 1-62 | SO$_2$Et | H | nBu | |
| 1-63 | SO$_2$Et | H | CH$_2$iPr | |
| 1-64 | SO$_2$Et | H | CH$_2$cPr | |
| 1-65 | SO$_2$Et | H | CH$_2$tBu | |
| 1-66 | SO$_2$Et | H | CH$_2$CH$_2$iPr | |
| 1-67 | SO$_2$Et | H | CH$_2$CH$_2$OMe | |
| 1-68 | SO$_2$Et | H | CH$_2$CH$_2$OEt | |
| 1-69 | SO$_2$Et | H | CH$_2$CH$_2$CH$_2$OMe | |
| 1-70 | SO$_2$Et | H | CH$_2$CH$_2$CH$_2$OMe | |

TABLE 2

Inventive compounds of the formula (I) in which $R^3$, $R^4$, $R^6$, $R^7$ and $R^8$ are each hydrogen and $R^5$ is methyl

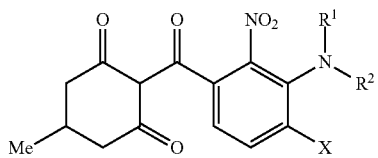

| No. | X | $R^1$ | $R^2$ | Physical data: $^1$H NMR: δ [CDCl$_3$] |
|---|---|---|---|---|
| 2-1 | Cl | H | H | 1.10 (d, 3H), 2.12 (dd, 1H), 2.28 (m, 1H), 2.4-2.52 (m, 2H), 2.78 (dd, 1H), 6.36 (d, 1H), 6.65 (s, br, 1H), 7.5 (d, 1H), 16.4 (s, 1H) |
| 2-2 | Cl | H | Me | 1.10 (d, 3H), 2.12 (dd, 1H), 2.28 (m, 1H), 2.4-2.52 (m, 2H), 2.78 (dd, 1H), 3.05 (d, 3H), 6.45 (d, 1H), 6.52 (s, br, 1H), 7.45 (d, 1H), 16.42 (s, br, 1H) |

TABLE 2-continued

Inventive compounds of the formula (I) in which $R^3$, $R^4$, $R^6$, $R^7$ and $R^8$ are each hydrogen and $R^5$ is methyl

| No. | X | $R^1$ | $R^2$ | Physical data: $^1$H NMR: δ [CDCl$_3$] |
|---|---|---|---|---|
| 2-3 | Cl | Me | Me | 1.10 (d, 3H), 2.12 (dd, 1H), 2.28 (m, 1H), 2.4-2.52 (m, 2H), 2.78 (dd, 1H), 2.85 (s, 6H), 6.85 (d, 1H), 7.5 (d, 1H), 16.4 (s, br, 1H) |
| 2-4 | Cl | H | Et | 1.10 (d, 3H), 1.25 (t, 3H), 2.12 (dd, 1H), 2.28 (m, 1H), 2.4-2.52 (m, 2H), 2.78 (dd, 1H), 3.4 (q, 2H), 6.38 (s, br, 1H), 6.48 (d, 1H), 7.46 (d, 1H), 16.45 (s, br, 1H) |
| 2-5 | Cl | H | nPr | 0.9 (t, 3H), 1.1 (d, 3H), 1.65 (m, 2H), 2.12 (dd, 1H), 2.3 (m, 1H), 2.48 (m, 2H), 2.78 (dd, 1H), 3.32 (t, 2H), 6.45 (d, 1H), 6.5 (s, br, 1H), 7.45 (d, 1H), 16.45 (s, 1H) |
| 2-6 | Cl | H | nBu | 0.92 (t, 3H), 1.10 (d, 3H), 1.39 (m, 2H), 1.6 (m, 2H), 2.12 (dd, 1H), 2.28 (m, 1H), 2.48 (m, 2H), 2.78 (dd, 1H), 3.35 (t, 2H), 6.45 (d, 1H), 7.45 (d, 1H), 16.42 (s, 1H) |
| 2-7 | Cl | H | CH$_2$iPr | 0.95 (d, 6H), 1.1 (d, 3H), 1.85 (m, 1H), 2.22 (dd, 1H), 2.43 (dd, 1H), 2.49 (dd, 1H), 2.79 (dd, 1H), 3.02 (d, 2H), 5.95 (s, 1H), 6.4 (d, 1H), 7.62 (d, 1H), 16.42 (s, 1H) |
| 2-8 | Cl | H | CH$_2$cPr | 0.25 (m, 2H), 0.55 (m, 2H), 1.05 (m, 1H), 1.1 (d, 3H), 2.22 (dd, 2H), 2.28 (m, 1H), 2.48 (m, 2H), 2.78 (dd, 1H), 3.18 (d, 2H), 6.48 (d, 1H), 6.55 (s, br, 1H), 7.45 (d, 1H), 16.45 (s, 1H) |
| 2-9 | Cl | H | CH$_2$tBu | 0.98 (s, 9H), 1.10 (d, 3H), 2.12 (dd, 1H), 2.28 (m, 1H), 2.48 (m, 2H), 2.78 (dd, 1H), 3.12 (s, 2H), 6.42 (d, 1H), 7.45 (d, 1H), 16.45 (s, 1H) |
| 2-10 | Cl | H | CH$_2$CH$_2$iPr | 0.9 (d, 6H), 1.1 (d, 3H), 1.51 (q, 2H), 1.68 (m, 1H), 2.12 (dd, 1H), 2.28 (m, 1H), 2.48 (m, 2H), 2.78 (dd, 1H), 3.35 (t, 2H), 6.45 (s, br, 1H), 6.45 (d, 1H), 7.45 (d, 1H), 16.42 (s, 1H) |
| 2-11 | Cl | H | CH$_2$CH$_2$OMe | |
| 2-12 | Cl | H | CH$_2$CH$_2$OEt | |
| 2-13 | Cl | H | CH$_2$CH$_2$CH$_2$OMe | 1.1 (d, 3H), 1.85 (m, 2H), 2.12 (dd, 1H), 2.28 (m, 1H), 2.42 (dd, 1H), 2.45 (dd, 1H), 2.78 (dd, 1H), 3.35 (s, 3H), 3.4 (m, 2H), 3.5 (t, 2H), 6.42 (d, 1H), 6.72 (t, br, 1H), 7.42 (d, 1H), 16.45 (s, 1H) |
| 2-14 | Cl | H | CH$_2$CH$_2$CH$_2$OMe | |
| 2-15 | Br | H | H | 1.10 (d, 3H), 2.1 (dd, 1H), 2.28 (m, 1H), 2.4 (dd, 1H), 2.5 (dd, 1H), 2.78 (dd, 1H), 6.3 (d, 1H), 6.3 (s, br, 1H), 7.68 (d, 1H), 16.4 (s, 1H) |
| 2-16 | Br | H | Me | 1.10 (d, 3H), 2.12 (dd, 1H), 2.28 (m, 1H), 2.4-2.52 (m, 2H), 2.78 (dd, 1H), 2.98 (s, 3H), 5.95 (s, br, 1H), 6.4 (d, 1H), 7.65 (d, 1H), 16.42 (s, 1H) |
| 2-17 | Br | Me | Me | |
| 2-18 | Br | H | Et | 1.10 (d, 3H), 1.25 (t, 3H), 2.12 (dd, 1H), 2.28 (m, 1H), 2.4-2.52 (m, 2H), 2.78 (dd, 1H), 3.5 (m, br, 2H), 5.79 (s, br, 1H), 6.42 (d, 1H), 7.65 (d, 1H), 16.42 (s, 1H) |
| 2-19 | Br | H | nPr | 0.9 (t, 3H), 1.1 (d, 3H), 1.65 (m, 2H), 2.12 (dd, 1H), 2.3 (m, 1H), 2.48 (m, 2H), 2.78 (dd, 1H), 3.18 (t, br, 2H), 5.88 (s, br, 1H), 6.42 (d, 1H), 7.65 (d, 1H), 16.42 (s, 1H) |
| 2-20 | Br | H | nBu | 0.92 (t, 3H), 1.10 (d, 3H), 1.39 (m, 2H), 1.6 (m, 2H), 2.12 (dd, 1H), 2.3 (m, 1H), 2.48 (m, 2H), 2.78 (dd, 1H), 3.2 (t, 2H), 6.42 (d, 1H), 7.65 (d, 1H), 16.42 (s, 1H) |
| 2-21 | Br | H | CH$_2$iPr | 0.95 (d, 6H), 1.1 (d, 3H), 1.85 (m, 1H), 2.22 (dd, 1H), 2.43 (dd, 1H), 2.49 (dd, 1H), 2.79 (dd, 1H), 3.02 (d, 2H), 5.95 (s, 1H), 6.4 (d, 1H), 7.62 (d, 1H), 16.42 (s, 1H) |
| 2-22 | Br | H | CH$_2$cPr | 0.25 (m, 2H), 0.55 (m, 2H), 1.05 (m, 1H), 1.1 (d, 3H), 2.22 (dd, 2H), 2.28 (m, 1H), 2.48 (m, 2H), 2.78 (dd, 1H), 3.18 (d, 2H), 6.48 (d, 1H), 7.45 (d, 1H), 16.45 (s, 1H) |
| 2-23 | Br | H | CH$_2$tBu | 0.98 (s, 9H), 1.10 (d, 3H), 2.12 (dd, 1H), 2.28 (m, 1H), 2.48 (m, 2H), 2.78 (dd, 1H), 3.12 (s, 2H), 6.42 (d, 1H), 7.45 (d, 1H), 16.45 (s, 1H) |

TABLE 2-continued

Inventive compounds of the formula (I) in which $R^3$, $R^4$, $R^6$, $R^7$ and $R^8$ are each hydrogen and $R^5$ is methyl

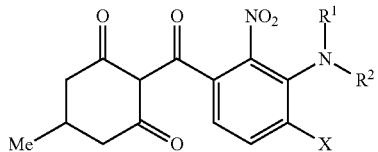

| No. | X | $R^1$ | $R^2$ | Physical data: $^1$H NMR: δ [CDCl$_3$] |
|---|---|---|---|---|
| 2-24 | Br | H | CH$_2$CH$_2$iPr | 0.9 (d, 6H), 1.1 (d, 3H), 1.51 (q, 2H), 1.68 (m, 1H), 2.12 (dd, 1H), 2.28 (m, 1H), 2.48 (m, 2H), 2.78 (dd, 1H), 3.22 (t, 2H), 5.85 (s, br, 1H), 6.42 (d, 1H), 7.65 (d, 1H), 16.42 (s, 1H) |
| 2-25 | Br | H | CH$_2$CH$_2$OMe | |
| 2-26 | Br | H | CH$_2$CH$_2$OEt | |
| 2-27 | Br | H | CH$_2$CH$_2$CH$_2$OMe | |
| 2-28 | Br | H | CH$_2$CH$_2$CH$_2$OMe | |
| 2-29 | F | H | H | |
| 2-30 | F | H | Me | |
| 2-31 | F | Me | Me | |
| 2-32 | F | H | Et | |
| 2-33 | F | H | nPr | |
| 2-34 | F | H | nBu | |
| 2-35 | F | H | CH$_2$iPr | |
| 2-36 | F | H | CH$_2$cPr | |
| 2-37 | F | H | CH$_2$tBu | |
| 2-38 | F | H | CH$_2$CH$_2$iPr | |
| 2-39 | F | H | CH$_2$CH$_2$OMe | |
| 2-40 | F | H | CH$_2$CH$_2$OEt | |
| 2-41 | F | H | CH$_2$CH$_2$CH$_2$OMe | |
| 2-42 | F | H | CH$_2$CH$_2$CH$_2$OMe | |
| 2-43 | SO$_2$Me | H | H | |
| 2-44 | SO$_2$Me | H | Me | |
| 2-45 | SO$_2$Me | Me | Me | |
| 2-46 | SO$_2$Me | H | Et | |
| 2-47 | SO$_2$Me | H | nPr | |
| 2-48 | SO$_2$Me | H | nBu | |
| 2-49 | SO$_2$Me | H | CH$_2$iPr | |
| 2-50 | SO$_2$Me | H | CH$_2$cPr | |
| 2-51 | SO$_2$Me | H | CH$_2$tBu | |
| 2-52 | SO$_2$Me | H | CH$_2$CH$_2$iPr | |
| 2-53 | SO$_2$Me | H | CH$_2$CH$_2$OMe | |
| 2-54 | SO$_2$Me | H | CH$_2$CH$_2$OEt | |
| 2-55 | SO$_2$Me | H | CH$_2$CH$_2$CH$_2$OMe | |
| 2-56 | SO$_2$Me | H | CH$_2$CH$_2$CH$_2$OMe | |
| 2-57 | SO$_2$Et | H | H | |
| 2-58 | SO$_2$Et | H | Me | |
| 2-59 | SO$_2$Et | Me | Me | |
| 2-60 | SO$_2$Et | H | Et | |
| 2-61 | SO$_2$Et | H | nPr | |
| 2-62 | SO$_2$Et | H | nBu | |
| 2-63 | SO$_2$Et | H | CH$_2$iPr | |
| 2-64 | SO$_2$Et | H | CH$_2$cPr | |
| 2-65 | SO$_2$Et | H | CH$_2$tBu | |
| 2-66 | SO$_2$Et | H | CH$_2$CH$_2$iPr | |
| 2-67 | SO$_2$Et | H | CH$_2$CH$_2$OMe | |
| 2-68 | SO$_2$Et | H | CH$_2$CH$_2$OEt | |
| 2-69 | SO$_2$Et | H | CH$_2$CH$_2$CH$_2$OMe | |
| 2-70 | SO$_2$Et | H | CH$_2$CH$_2$CH$_2$OMe | |

TABLE 3

Inventive compounds of the formula (I) in which $R^5$, $R^6$, $R^7$ and $R^8$ are each hydrogen and $R^3$ and $R^4$ are each methyl

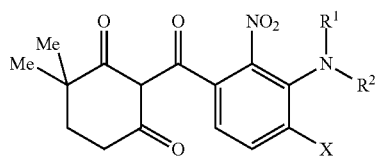

| No. | X | $R^1$ | $R^2$ | Physical data: $^1$H NMR: δ [CDCl$_3$] |
|---|---|---|---|---|
| 3-1 | Cl | H | H | 1.10 and 1.38 (s, 6H), 1.85 (m, 2H), 2.4 and 2.78 (m, 2H), 6.45 and 6.46 (d, 1H), 7.51 (d,d 1H), 16.32 and 17 (s, 1H) |
| 3-2 | Cl | H | Me | 1.10 and 1.38 (s, 6H), 1.85 (m, 2H), 2.43 and 2.78 (m, 2H), 3.04 and 3.05 (s, 3H), 6.42 and 6.44 (d, 1H), 7.45 (d,d 1H), 16.32 and 17 (s, 1H) |
| 3-3 | Cl | Me | Me | 1.10 and 1.38 (s, 6H), 1.85 (m, 2H), 2.43 and 2.78 (m, 2H), 2.85 (s, 6H), 6.85 and 6.88 (d, 1H), 7.5 (d, 1H), 16.3 and 16.9 (s, 1H) |
| 3-4 | Cl | H | Et | 1.10 and 1.38 (s, 6H), 1.25 (m, 3H), 1.85 (m, 2H), 2.43 and 2.78 (m, 2H), 3.38 (m, 2H), 6.25 and 6.32 (s, br, 1H), 6.46 (d,d 1H), 7.45 (d,d 1H), 16.32 and 16.98 (s, br, 1H) |
| 3-5 | Cl | H | nPr | 0.96 (t, 3H), 1.08 and 1.38 (s, 6H), 1.62 (m, 2H), 1.85 (m, 2H), 2.45 and 2.78 (m, 2H), 3.30 (m, 2H), 6.45 (d,d 1H), 7.45 (d,d, 1H), 16.35 and 17.0 (s, br, 1H) |
| 3-6 | Cl | H | nBu | 0.92 (t, 3H), 1.10 and 1.38 (s, 6H), 1.39 (m, 2H), 1.6 (m, 2H), 1.85 (m, 2H), 2.43 and 2.78 (m, 2H), 3.32 (m, 2H), 6.45 (d,d 1H), 7.45 (d,d 1H), 16.35 and 17.0 (s, 1H) |
| 3-7 | Cl | H | CH$_2$iPr | 0.95 (d, 6H), 1.10 and 1.38 (s, 6H), 1.85 (m, 1H), 1.85 and 2.43 (m, 2H), 2.78 (m, 2H), 3.15 and 3.18 (d, 2H), 6.45 (d,d, 1H), 7.45 (d,d, 1H), 16.35 and 17.0 (s, 1H) |
| 3-8 | Cl | H | CH$_2$cPr | 0.25 (m, 2H), 0.55 (m, 2H), 1.05 (m, 1H), 1.10 and 1.38 (s, 6H), 1.85 (m, 2H), 2.43 and 2.78 (t, 2H), 3.15 (m, 2H), 6.4 and 6.48 (s, br, 1H), 6.48 (d,d 1H), 7.45 (d,d 1H), 16.35 and 16.98 (s, 1H) |
| 3-9 | Cl | H | CH$_2$tBu | 0.98 (s, 9H), 1.10 and 1.38 (s, 6H), 1.85 (m, 2H), 2.43 and 2.78 (m, 2H), 3.1 (m, 2H), 6.4 and 6.48 (s, br, 1H), 6.43 (d,d 1H), 7.45 (d,d 1H), 16.35 and 17.0 (s, 1H) |
| 3-10 | Cl | H | CH$_2$CH$_2$iPr | 0.92 (d, 6H), 1.10 and 1.38 (s, 6H), 1.52 (m, 2H), 1.65 (m, 1H), 1.85 (m, 2H), 2.43 and 2.78 (m, 2H), 3.35 (m, 2H), 6.3 and 6.4 (t, br, 1H), 6.45 (d,d 1H), 7.45 (d,d 1H), 16.35 and 16.98 (s, 1H) |
| 3-11 | Cl | H | CH$_2$CH$_2$OMe | |
| 3-12 | Cl | H | CH$_2$CH$_2$OEt | |
| 3-13 | Cl | H | CH$_2$CH$_2$CH$_2$OMe | |
| 3-14 | Cl | H | CH$_2$CH$_2$CH$_2$OMe | |
| 3-15 | Br | H | H | 1.09 and 1.38 (s, 6H), 1.85 (m, 2H), 2.4 and 2.78 (m, 2H), 6.3 (d,d 1H), 6.7 (s, br, 2H), 7.68 (d,d 1H), 16.3 and 16.98 (s, br, 1H) |
| 3-16 | Br | H | Me | 1.10 and 1.38 (s, 6H), 1.85 (m, 2H), 2.43 and 2.78 (m, 2H), 2.95 (d, 3H), 6.4 (d,d 1H), 7.62 (d,d 1H), 16.32 and 16.98 (s, br, 1H) |
| 3-17 | Br | Me | Me | δ [MeOD] = 1.2 (s, 6H), 1.9 (t, 2H), 2.75 (m, 2H), 2.85 (s, 6H), 6.95 (d, 1H), 7.8 (d, 1H) |
| 3-18 | Br | H | Et | 1.10 and 1.38 (s, 6H), 1.25 (m, 3H), 1.85 (m, 2H), 2.43 and 2.78 (m, 2H), 3.25 (m, 2H), 5.65 and 5.75 (s, br, 1H), 6.42 (d,d 1H), 7.65 (d,d 1H), 16.32 and 16.98 (s, br, 1H) |
| 3-19 | Br | H | nPr | 0.96 (t, 3H), 1.1 and 1.38 (s, 6H), 1.62 (m, 2H), 1.85 (m, 2H), 2.43 and 2.78 (m, 2H), 3.15 (m, 2H), 5.75 and 5.85 (s, br, 1H) 6.42 (d,d 1H), 7.62 (d,d, 1H), 16.35 and 16.98 (s, br, 1H) |
| 3-20 | Br | H | nBu | 0.92 (t, 3H), 1.10 and 1.38 (s, 6H), 1.39 (m, 2H), 1.6 (m, 2H), 1.85 (m, 2H), 2.43 and 2.78 (m, 2H), 3.18 (t, 2H), 6.4 (d,d 1H), 7.65 (d,d 1H), 16.35 and 17.0 (s, 1H) |
| 3-21 | Br | H | CH$_2$iPr | 0.95 (d, 6H), 1.10 and 1.38 (s, 6H), 1.85 (m, 1H), 1.85 and 2.43 (m, 2H), 2.78-3.0 (m, 2H), 2.99 (m, 2H), 5.82 and 5.9 (t, br, 1H), 6.4 (d,d, 1H), 7.65 (d,d, 1H), 16.45 and 16.98 (s, 1H) |

TABLE 3-continued

Inventive compounds of the formula (I) in which $R^5$, $R^6$, $R^7$ and $R^8$ are each hydrogen and $R^3$ and $R^4$ are each methyl

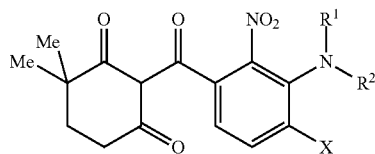

| No. | X | $R^1$ | $R^2$ | Physical data: $^1$H NMR: δ [CDCl$_3$] |
|---|---|---|---|---|
| 3-22 | Br | H | CH$_2$cPr | 0.25 (m, 2H), 0.55 (m, 2H), 1.05 (m, 1H), 1.10 and 1.38 (s, 6H), 1.85 and 2.43 (m, 2H), 2.78-2.95 (m, 2H), 3.02 (m, 2H), 6.48 (d,d 1H), 7.65 (d,d 1H), 16.35 and 16.98 (s, 1H) |
| 3-23 | Br | H | CH$_2$tBu | 0.98 (s, 9H), 1.10 and 1.38 (s, 6H), 1.85 (m, 2H), 2.43 and 2.78 (m, 2H), 2.85-2.95 (m, 2H), 5.78 and 5.88 (t, br, 1H), 6.4 (d,d 1H), 7.65 (d,d 1H), 16.35 and 17.0 (s, 1H) |
| 3-24 | Br | H | CH$_2$CH$_2$iPr | 0.92 (d, 6H), 1.10 and 1.38 (s, 6H), 1.5 (m, 2H), 1.65 (m, 1H), 1.85 (m, 2H), 2.43 and 2.78 (m, 2H), 3.18 (m, 2H), 6.41 (d,d 1H), 7.63 (d,d 1H), 16.35 and 16.98 (s, 1H) |
| 3-25 | Br | H | CH$_2$CH$_2$OMe | |
| 3-26 | Br | H | CH$_2$CH$_2$OEt | |
| 3-27 | Br | H | CH$_2$CH$_2$CH$_2$OMe | |
| 3-28 | Br | H | CH$_2$CH$_2$CH$_2$OMe | |
| 3-29 | F | H | H | 1.08 and 1.38 (s, 3H), 1.85 (m, 2H), 2.4 and 2.78 (t, 2H), 6.2 (s, br, 2H), 6.32 (m, 1H), 7.2 (m, 1H), 16.42 and 17.1 (s, 1H) |
| 3-30 | F | H | Me | |
| 3-31 | F | Me | Me | |
| 3-32 | F | H | Et | |
| 3-33 | F | H | nPr | |
| 3-34 | F | H | nBu | |
| 3-35 | F | H | CH$_2$iPr | |
| 3-36 | F | H | CH$_2$cPr | |
| 3-37 | F | H | CH$_2$tBu | |
| 3-38 | F | H | CH$_2$CH$_2$iPr | |
| 3-39 | F | H | CH$_2$CH$_2$OMe | |
| 3-40 | F | H | CH$_2$CH$_2$OEt | |
| 3-41 | F | H | CH$_2$CH$_2$CH$_2$OMe | |
| 3-42 | F | H | CH$_2$CH$_2$CH$_2$OMe | |
| 3-43 | SO$_2$Me | H | H | 1.02 and 1.32 (s, 3H), 1.8 (m, 2H), 2.38 and 2.75 (t, 2H), 3.07 and 3.08 (s, 3H), 6.42 and 6.46 (d, 2H), 7.52 (s, 2H), 8.01 (d, 2H), 15.89 and 16.58 (s, 1H) |
| 3-44 | SO$_2$Me | H | Me | δ [MeOD] = 1.2 (s, 6H), 1.8 (t, 2H), 2.32 (t, 2H), 2.68 (s, 3H), 3.1 (s, 3H), 6.51 (d, 1H), 7.85 (d, 1H) |
| 3-45 | SO$_2$Me | Me | Me | |
| 3-46 | SO$_2$Me | H | Et | |
| 3-47 | SO$_2$Me | H | nPr | |
| 3-48 | SO$_2$Me | H | nBu | |
| 3-49 | SO$_2$Me | H | CH$_2$iPr | |
| 3-50 | SO$_2$Me | H | CH$_2$cPr | |
| 3-51 | SO$_2$Me | H | CH$_2$tBu | |
| 3-52 | SO$_2$Me | H | CH$_2$CH$_2$iPr | |
| 3-53 | SO$_2$Me | H | CH$_2$CH$_2$OMe | |
| 3-54 | SO$_2$Me | H | CH$_2$CH$_2$OEt | |
| 3-55 | SO$_2$Me | H | CH$_2$CH$_2$CH$_2$OMe | |
| 3-56 | SO$_2$Me | H | CH$_2$CH$_2$CH$_2$OMe | |
| 3-57 | SO$_2$Et | H | H | |
| 3-58 | SO$_2$Et | H | Me | |
| 3-59 | SO$_2$Et | Me | Me | |
| 3-60 | SO$_2$Et | H | Et | |
| 3-61 | SO$_2$Et | H | nPr | |
| 3-62 | SO$_2$Et | H | nBu | |
| 3-63 | SO$_2$Et | H | CH$_2$iPr | |
| 3-64 | SO$_2$Et | H | CH$_2$cPr | |
| 3-65 | SO$_2$Et | H | CH$_2$tBu | |
| 3-66 | SO$_2$Et | H | CH$_2$CH$_2$iPr | |
| 3-67 | SO$_2$Et | H | CH$_2$CH$_2$OMe | |
| 3-68 | SO$_2$Et | H | CH$_2$CH$_2$OEt | |
| 3-69 | SO$_2$Et | H | CH$_2$CH$_2$CH$_2$OMe | |
| 3-70 | SO$_2$Et | H | CH$_2$CH$_2$CH$_2$OMe | |

TABLE 4

Inventive compounds of the formula (I) in which $R^4$, $R^5$, $R^6$ and $R^7$ are each hydrogen and $R^3$ and $R^8$ are $CH_2CH_2$

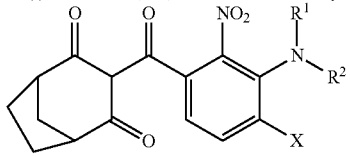

| No. | X | $R^1$ | $R^2$ | Physical data: $^1$H NMR: δ [CDCl$_3$] |
|---|---|---|---|---|
| 4-1 | Cl | H | H | 1.68 (m, 2H), 1.98-2.25 (m, 4H), 2.82 (m, 1H), 3.1 (m, 1H), 6.39 (s, 1H), 6.62 (s, br, 2H), 7.51 (d, 1H), 16.3 (s, 1H) |
| 4-2 | Cl | H | Me | 1.7 (m, 2H), 1.98-2.25 (m, 4H), 2.85 (m, 1H), 3.05 (s, 3H), 3.12 (m, 1H), 6.49 (d, 1H), 7.46 (d, 1H), 16.38 (s, 1H) |
| 4-3 | Cl | Me | Me | 1.68 (m, 2H), 1.98-2.25 (m, 4H), 2.82 (s, 6H), 2.89 (m, 1H), 3.12 (m, 1H), 6.9 (d, 1H), 7.5 (d, 1H), 16.4 (s, 1H) |
| 4-4 | Cl | H | Et | 1.25 (t, 3H), 1.68 (m, 2H), 1.98-2.25 (m, 4H), 2.89 (m, 1H), 3.12 (m, 1H), 3.48 (q, 3H), 6.5 (d, 1H), 7.485 (d, 1H), 16.4 (s, 1H) |
| 4-5 | Cl | H | nPr | 0.95 (t, 3H), 1.65 (q, 2H), 1.7 (m, 2H), 1.98-2.25 (m, 4H), 2.85 (m, 1H), 3.1 (m, 1H), 3.3 (t, 2H), 6.38 (s, 1H), 6.5 (d, 1H), 7.46 (d, 1H), 16.4 (s, br, 1H) |
| 4-6 | Cl | H | nBu | 0.92 (t, 3H), 1.38 (m, 2H), 1.6 (m, 2H), 1.7 (m, 2H), 1.98-2.25 (m, 4H), 2.85 (m, 1H), 3.1 (m, 1H), 3.33 (q, 2H), 6.48 (d, 1H), 7.45 (d, 1H), 16.38 (s, br, 1H) |
| 4-7 | Cl | H | CH$_2$iPr | 0.98 (d, 6H), 1.7 (m, 2H), 1.85 (m, 1H), 1.98-2.25 (m, 4H), 2.85 (m, 1H), 3.1 (m, 1H), 3.15 (d, 2H), 6.48 (d, 1H), 7.45 (d, 1H), 16.4 (s, 1H) |
| 4-8 | Cl | H | CH$_2$cPr | 0.25 (m, 2H), 0.55 (m, 2H), 1.05 (m, 1H), 1.7 (m, 2H), 1.98-2.25 (m, 4H), 2.85 (m, 1H), 3.1 (m, 1H), 3.15 (d, 2H), 6.4 (s, br, 1H), 6.5 (d, 1H), 7.45 (d, 1H), 16.38 (s, 1H) |
| 4-9 | Cl | H | CH$_2$tBu | 0.98 (s, 9H), 1.7 (m, 2H), 1.98-2.25 (m, 4H), 2.85 (m, 1H), 3.1 (m, 1H), 6.48 (d, 1H), 7.45 (d, 1H), 16.38 (s, 1H) |
| 4-10 | Cl | H | CH$_2$CH$_2$iPr | 0.90 (d, 6H), 1.5 (m, 2H), 1.7 (m, 1H), 1.7 (m, 2H), 1.98-2.25 (m, 4H), 2.85 (m, 1H), 3.1 (m, 1H), 3.35 (m, 2H), 6.35 (s, br, 1H), 6.5 (d, 1H), 7.45 (d, 1H), 16.38 (s, 1H) |
| 4-11 | Cl | H | CH$_2$CH$_2$OMe | |
| 4-12 | Cl | H | CH$_2$CH$_2$OEt | |
| 4-13 | Cl | H | CH$_2$CH$_2$CH$_2$OMe | 1.7 (m, 2H), 1.85 (m, 2H), 1.98-2.25 (m, 4H), 2.85 (m, 1H), 3.1 (m, 1H), 3.5 (s, 3H), 3.8 (t, 2H), 3.48 (m, 2H), 6.48 (d, 1H), 7.45 (d, 1H), 16.4 (s, br, 1H) |
| 4-14 | Cl | H | CH$_2$CH$_2$CH$_2$OMe | |
| 4-15 | Br | H | H | 1.7 (m, 2H), 1.98-2.25 (m, 4H), 2.81 (m, 1H), 3.1 (m, 1H), 6.35 (d, 1H), 6.68 (s, br, 2H), 7.68 (d, 1H), 16.28 (s, 1H) |
| 4-16 | Br | H | Me | 1.72 (m, 2H), 1.98-2.25 (m, 4H), 2.88 (m, 1H), 2.95 (s, 3H), 3.12 (m, 1H), 6.42 (d, 1H), 7.62 (d, 1H), 16.38 (s, br, 1H) |
| 4-17 | Br | Me | Me | 1.72 (m, 2H), 1.98-2.25 (m, 4H), 2.82 (s, 6H), 2.9 (m, 1H), 3.12 (m, 1H), 6.82 (d, 1H), 7.72 (d, 1H), 16.4 (s, br, 1H) |
| 4-18 | Br | H | Et | 1.25 (t, 3H), 1.7 (m, 2H), 1.98-2.25 (m, 4H), 2.85 (m, 1H), 3.1 (m, 1H), 3.25 (q, 2H), 5.7 (s, br, 1H), 6.48 (d, 1H), 7.65 (d, 1H), 16.38 (s, br, 1H) |
| 4-19 | Br | H | nPr | 0.98 (t, 3H), 1.62 (m, 2H), 1.7 (m, 2H), 1.98-2.25 (m, 4H), 2.85 (m, 1H), 3.1 (m, 1H), 3.15 (t, 2H), 5.8 (s, br, 1H), 6.48 (d, 1H), 7.65 (d, 1H), 16.38 (s, br, 1H) |
| 4-20 | Br | H | nBu | 0.92 (t, 3H), 1.38 (m, 2H), 1.6 (m, 2H), 1.7 (m, 2H), 1.98-2.25 (m, 4H), 2.85 (m, 1H), 3.1 (m, 1H), 3.28 (q, 2H), 5.78 (s, br, 1H), 6.45 (d, 1H), 7.65 (d, 1H), 16.38 (s, br, 1H) |
| 4-21 | Br | H | CH$_2$iPr | 0.98 (d, 6H), 1.7 (m, 2H), 1.85 (m, 1H), 1.98-2.25 (m, 4H), 2.85 (m, 1H), 3.0 (d, 2H), 3.1 (m, 1H), 5.7 (s, br, 1H), 6.45 (d, 1H), 7.65 (d, 1H), 16.38 (s, 1H) |

TABLE 4-continued

Inventive compounds of the formula (I) in which $R^4$, $R^5$, $R^6$ and $R^7$ are each hydrogen and $R^3$ and $R^8$ are $CH_2CH_2$

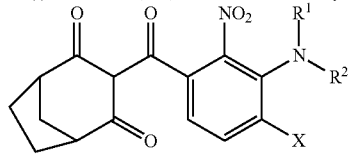

| No. | X | $R^1$ | $R^2$ | Physical data: $^1$H NMR: δ [CDCl$_3$] |
|---|---|---|---|---|
| 4-22 | Br | H | CH$_2$cPr | 0.25 (m, 2H), 0.55 (m, 2H), 1.05 (m, 1H), 1.7 (m, 2H), 1.98-2.25 (m, 4H), 2.85 (m, 1H), 3.1 (m, 1H), 3.15 (d, 2H), 6.4 (s, br, 1H), 6.5 (d, 1H), 7.45 (d, 1H), 16.38 (s, 1H) |
| 4-23 | Br | H | CH$_2$tBu | 0.98 (s, 9H), 1.7 (m, 2H), 1.98-2.25 (m, 4H), 2.85 (m, 1H), 3.1 (m, 1H), 6.48 (d, 1H), 7.45 (d, 1H), 16.4 (s, 1H) |
| 4-24 | Br | H | CH$_2$CH$_2$iPr | 0.90 (d, 6H), 1.5 (m, 2H), 1.7 (m, 1H), 1.7 (m, 2H), 1.98-2.25 (m, 4H), 2.85 (m, 1H), 3.1 (m, 1H), 3.22 (m, 2H), 5.88 (t, br, 1H), 6.42 (d, 1H), 7.65 (d, 1H), 16.48 (s, 1H) |
| 4-25 | Br | H | CH$_2$CH$_2$OMe | |
| 4-26 | Br | H | CH$_2$CH$_2$OEt | |
| 4-27 | Br | H | CH$_2$CH$_2$CH$_2$OMe | |
| 4-28 | Br | H | CH$_2$CH$_2$CH$_2$OMe | |
| 4-29 | F | H | H | 1.7 (m, 2H), 1.98-2.25 (m, 4H), 2.82 (m, 1H), 3.1 (m, 1H), 6.2 (s, br, 2H), 6.38 (dd, 1H), 7.2 (dd, 1H), 16.42 (s, 1H) |
| 4-30 | F | H | Me | δ [MeOD] = 1.65 (m, 6H), 2.82 (m, 2H), 2.95 (s, 3H), 6.78 (d, 1H), 7.88 (dd, 1H) |
| 4-31 | F | Me | Me | δ [MeOD] = 1.4 (m, 2H), 1.65 (m, 4H), 2.85 (m, 2H), 3.12 (s, 6H), 6.92 (dd, 1H), 7.88 (dd, 1H) |
| 4-32 | F | H | Et | |
| 4-33 | F | H | nPr | |
| 4-34 | F | H | nBu | |
| 4-35 | F | H | CH$_2$iPr | |
| 4-36 | F | H | CH$_2$cPr | |
| 4-37 | F | H | CH$_2$tBu | |
| 4-38 | F | H | CH$_2$CH$_2$iPr | |
| 4-39 | F | H | CH$_2$CH$_2$OMe | |
| 4-40 | F | H | CH$_2$CH$_2$OEt | |
| 4-41 | F | H | CH$_2$CH$_2$CH$_2$OMe | |
| 4-42 | F | H | CH$_2$CH$_2$CH$_2$OMe | |
| 4-43 | SO$_2$Me | H | H | 1.7 (m, 2H), 1.98-2.25 (m, 4H), 2.85 (m, 1H), 3.1 (m, 1H), 3.15 (s, 3H), 6.55 (d, 1H), 8.09 (d, 1H), 15.92 (s, br, 1H) |
| 4-44 | SO$_2$Me | H | Me | δ [MeOD] = 1.4 (m, 2H), 1.65 (m, 4H), 2.85 (m, 2H), 2.88 (s, 3H), 3.18 (s, 3H), 7.25 (d, 1H), 7.98 (d, 1H) |
| 4-45 | SO$_2$Me | Me | Me | 1.7 (m, 2H), 1.98-2.25 (m, 4H), 2.85 (m, 1H), 2.86 (s, 6H), 3.1 (m, 1H), 3.15 (s, 3H), 6.55 (d, 1H), 8.09 (d, 1H), 15.92 (s, br, 1H) |
| 4-46 | SO$_2$Me | H | Et | |
| 4-47 | SO$_2$Me | H | nPr | |
| 4-48 | SO$_2$Me | H | nBu | |
| 4-49 | SO$_2$Me | H | CH$_2$iPr | |
| 4-50 | SO$_2$Me | H | CH$_2$cPr | |
| 4-51 | SO$_2$Me | H | CH$_2$tBu | |
| 4-52 | SO$_2$Me | H | CH$_2$CH$_2$iPr | |
| 4-53 | SO$_2$Me | H | CH$_2$CH$_2$OMe | |
| 4-54 | SO$_2$Me | H | CH$_2$CH$_2$OEt | |
| 4-55 | SO$_2$Me | H | CH$_2$CH$_2$CH$_2$OMe | |
| 4-56 | SO$_2$Me | H | CH$_2$CH$_2$CH$_2$OMe | |
| 4-57 | SO$_2$Et | H | H | |
| 4-58 | SO$_2$Et | H | Me | |
| 4-59 | SO$_2$Et | Me | Me | |
| 4-60 | SO$_2$Et | H | Et | |
| 4-61 | SO$_2$Et | H | nPr | |
| 4-62 | SO$_2$Et | H | nBu | |
| 4-63 | SO$_2$Et | H | CH$_2$iPr | |
| 4-64 | SO$_2$Et | H | CH$_2$cPr | |
| 4-65 | SO$_2$Et | H | CH$_2$tBu | |
| 4-66 | SO$_2$Et | H | CH$_2$CH$_2$iPr | |
| 4-67 | SO$_2$Et | H | CH$_2$CH$_2$OMe | |
| 4-68 | SO$_2$Et | H | CH$_2$CH$_2$OEt | |
| 4-69 | SO$_2$Et | H | CH$_2$CH$_2$CH$_2$OMe | |
| 4-70 | SO$_2$Et | H | CH$_2$CH$_2$CH$_2$OMe | |

TABLE 5

Inventive compounds of the formula (I) in which $R^3$, $R^4$, $R^7$ and $R^8$ are each methyl and $R^5$ and $R^6$ are =O

| No. | X | $R^1$ | $R^2$ | Physical data: $^1$H NMR: δ [CDCl$_3$] |
|---|---|---|---|---|
| 5-1 | Cl | H | H | 1.28 (s, 6H), 1.55 (s, 6H), 6.42 (d, 1H), 6.68 (s, br, 1H), 7.55 (d, 1H), 16.9 (s, 1H) |
| 5-2 | Cl | H | Me | 1.3 (s, 6H), 1.55 (s, 6H), 3.08 (s, 3H), 6.48 (d, 1H), 7.48 (d, 1H), 16.9 (s, 1H) |
| 5-3 | Cl | Me | Me | 1.34 (s, 6H), 1.55 (s, 6H), 2.85 (s, 6H), 6.88 (d, 1H), 7.52 (d, 1H), 16.9 (s, 1H) |
| 5-4 | Cl | H | Et | |
| 5-5 | Cl | H | nPr | |
| 5-6 | Cl | H | nBu | |
| 5-7 | Cl | H | CH$_2$iPr | |
| 5-8 | Cl | H | CH$_2$cPr | |
| 5-9 | Cl | H | CH$_2$tBu | |
| 5-10 | Cl | H | CH$_2$CH$_2$iPr | |
| 5-11 | Cl | H | CH$_2$CH$_2$OMe | |
| 5-12 | Cl | H | CH$_2$CH$_2$OEt | |
| 5-13 | Cl | H | CH$_2$CH$_2$CH$_2$OMe | |
| 5-14 | Cl | H | CH$_2$CH$_2$CH$_2$OMe | |
| 5-15 | Br | H | H | |
| 5-16 | Br | H | Me | |
| 5-17 | Br | Me | Me | |
| 5-18 | Br | H | Et | |
| 5-19 | Br | H | nPr | |
| 5-20 | Br | H | nBu | |
| 5-21 | Br | H | CH$_2$iPr | |
| 5-22 | Br | H | CH$_2$cPr | |
| 5-23 | Br | H | CH$_2$tBu | |
| 5-24 | Br | H | CH$_2$CH$_2$iPr | |
| 5-25 | Br | H | CH$_2$CH$_2$OMe | |
| 5-26 | Br | H | CH$_2$CH$_2$OEt | |
| 5-27 | Br | H | CH$_2$CH$_2$CH$_2$OMe | |
| 5-28 | Br | H | CH$_2$CH$_2$CH$_2$OMe | |
| 5-29 | F | H | H | |
| 5-30 | F | H | Me | |
| 5-31 | F | Me | Me | |
| 5-32 | F | H | Et | |
| 5-33 | F | H | nPr | |
| 5-34 | F | H | nBu | |
| 5-35 | F | H | CH$_2$iPr | |
| 5-36 | F | H | CH$_2$cPr | |
| 5-37 | F | H | CH$_2$tBu | |
| 5-38 | F | H | CH$_2$CH$_2$iPr | |
| 5-39 | F | H | CH$_2$CH$_2$OMe | |
| 5-40 | F | H | CH$_2$CH$_2$OEt | |
| 5-41 | F | H | CH$_2$CH$_2$CH$_2$OMe | |
| 5-42 | F | H | CH$_2$CH$_2$CH$_2$OMe | |
| 5-43 | SO$_2$Me | H | H | |
| 5-44 | SO$_2$Me | H | Me | |
| 5-45 | SO$_2$Me | Me | Me | |
| 5-46 | SO$_2$Me | H | Et | |
| 5-47 | SO$_2$Me | H | nPr | |
| 5-48 | SO$_2$Me | H | nBu | |
| 5-49 | SO$_2$Me | H | CH$_2$iPr | |
| 5-50 | SO$_2$Me | H | CH$_2$cPr | |
| 5-51 | SO$_2$Me | H | CH$_2$tBu | |
| 5-52 | SO$_2$Me | H | CH$_2$CH$_2$iPr | |
| 5-53 | SO$_2$Me | H | CH$_2$CH$_2$OMe | |
| 5-54 | SO$_2$Me | H | CH$_2$CH$_2$OEt | |
| 5-55 | SO$_2$Me | H | CH$_2$CH$_2$CH$_2$OMe | |
| 5-56 | SO$_2$Me | H | CH$_2$CH$_2$CH$_2$OMe | |
| 5-57 | SO$_2$Et | H | H | |
| 5-58 | SO$_2$Et | H | Me | |
| 5-59 | SO$_2$Et | Me | Me | |
| 5-60 | SO$_2$Et | H | Et | |
| 5-61 | SO$_2$Et | H | nPr | |
| 5-62 | SO$_2$Et | H | nBu | |
| 5-63 | SO$_2$Et | H | CH$_2$iPr | |

TABLE 5-continued

Inventive compounds of the formula (I) in which $R^3$, $R^4$, $R^7$ and $R^8$ are each methyl and $R^5$ and $R^6$ are =O

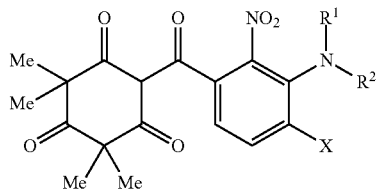

| No. | X | $R^1$ | $R^2$ | Physical data: $^1$H NMR: δ [CDCl$_3$] |
|---|---|---|---|---|
| 5-64 | SO$_2$Et | H | CH$_2$cPr | |
| 5-65 | SO$_2$Et | H | CH$_2$tBu | |
| 5-66 | SO$_2$Et | H | CH$_2$CH$_2$iPr | |
| 5-67 | SO$_2$Et | H | CH$_2$CH$_2$OMe | |
| 5-68 | SO$_2$Et | H | CH$_2$CH$_2$OEt | |
| 5-69 | SO$_2$Et | H | CH$_2$CH$_2$CH$_2$OMe | |
| 5-70 | SO$_2$Et | H | CH$_2$CH$_2$CH$_2$OMe | |

B. Formulation Examples a) A dust is obtained by mixing 10 parts by weight of a compound of the formula (I) and/or a salt thereof and 90 parts by weight of talc as inert substance and comminuting the mixture in a hammer mill.

b) A wettable powder which is readily dispersible in water is obtained by mixing 25 parts by weight of a compound of the formula (I) and/or a salt thereof, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A readily water-dispersible dispersion concentrate is obtained by mixing 20 parts by weight of a compound of the formula (I) and/or a salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I) and/or a salt thereof, 75 parts by weight of cyclohexanone as solvent and 10 parts by weight of oxethylated nonylphenol as emulsifier.

e) Water-dispersible granules are obtained by mixing 75 parts by weight of a compound of the formula (I) and/or a salt thereof, 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill, and granulating the powder in a fluidized bed by spraying on water as granulating liquid.

f) Water-dispersible granules are also obtained by homogenizing and precomminuting, in a colloid mill, 25 parts by weight of a compound of the formula (I) and/or a salt thereof, 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance nozzle.

C. Biological Examples

1. Pre-Emergence Herbicidal Action Against Harmful Plants

Seeds of monocotyledonous or dicotyledonous weed plants or crop plants are placed in wood-fiber pots in sandy loam and covered with soil. The compounds according to the invention, formulated in the form of wettable powders (WP) or as emulsion concentrates (EC), are then applied as aqueous suspension or emulsion at a water application rate of 600 to 800 l/ha (converted) with the addition of 0.2% of wetting agent to the surface of the covering soil. After the treatment, the pots are placed in a greenhouse and kept under good growth conditions for the test plants. The visual assessment of the damage to the test plants is carried out after a trial period of 3 weeks by comparison with untreated controls (herbicidal activity in percent (%): 100% activity=the plants have died, 0% activity=like control plants). In this test, for example, the compounds No. 1-1, 4-1, 1-2, 4-2, 3-1, 1-3, 3-2, 3-15, 4-15, 1-15, 1-16, 3-16, 4-16, 1-16, 4-17, 4-29, 1-43, 3-43, 4-43, 5-2, 5-3, 4-3, 3-44, 2-1, 1-17, 3-17, 4-45, 1-4, 4-4, 2-4, 1-5, 3-5, 4-5, 1-19, 4-19, 4-7, 1-18, 4-21, 1-9, 1-7, 3-8 and 1-8, at an application rate of 320 g/ha, each exhibit an activity of at least 90% against Abuthilon theophrasti and Echinocloa crus galli.

2. Post-Emergence Herbicidal Action Against Harmful Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention, formulated in the form of wettable powders (WP) or as emulsion concentrates (EC), are then sprayed as aqueous suspension or emulsion at a water application rate of 600 to 800 l/ha (converted) with the addition of 0.2% of wetting agent onto the green parts of the plants. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=like control plants). In this test, for example, the compounds No. 1-1, 4-1, 1-2, 3-1, 1-3, 3-2, 3-15, 4-15, 1-15, 3-16, 4-17, 4-29, 1-43, 3-43, 4-43, 2-1, 5-3, 4-3, 2-1, 1-17, 3-17, 4-45, 1-4, 4-4, 2-4, 1-5, 3-5, 4-5, 1-19, 3-19, 4-7, 1-18, 3-18, 4-18, 4-6, 1-7, 1-5, 2-6, 2-15, 4-20, 3-8, 2-8 and 1-8, at an application rate of 80 g/ha, each exhibit an activity of at least 80% against Abuthilon theophrasti und Echinocloa crus galli. p

What is claimed is:

1. A compound of the formula (I) and/or a salt thereof

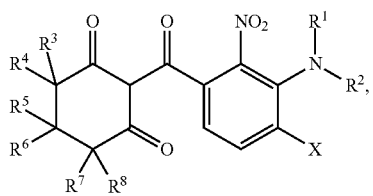

in which

X is halogen, ethylsulfonyl, methylsulfonyl, 1,2,4-triazol-1-yl or 1,2,4-triazol-4-yl, $R^1$ and $R^2$ are independently of one another each hydrogen, $(C_1-C_6)$-alkyl, $(C_2-C_6)$-alkenyl, $(C_2-C_6)$-alkynyl, halo-$(C_1-C_6)$-alkyl, halo-$(C_1-C_6)$-alkenyl, halo-$(C_1-C_6)$-alkynyl, $(C_3-C_6)$-cycloalkyl-$(C_1-C_6)$-alkyl, $(C_3-C_6)$-cycloalkenyl-$(C_1-C_6)$-alkyl, $(C_1-C_6)$-alkoxy-$(C_1-C_6)$-alkyl, $R^4$ and $R^7$ independently of one another are each hydrogen or methyl, $R^3$ and $R^8$ independently of one another are each hydrogen or methyl, or $R^3$ and $R^8$ together form the group $CH_2CH_2$ or CH=CH, $R^5$ and $R^6$ independently of one another are each hydrogen or methyl, or $R^5$ and $R^6$, together with the carbon atom to which they are attached, form the group C=O.

2. The compound and/or salt as claimed in claim 1, in which

X is chlorine, bromine, fluorine or methylsulfonyl, $R^1$ and $R^2$ are independently of one another each hydrogen, $(C_1-C_6)$-alkyl, halo-$(C_1-C_6)$-alkyl, halo-$(C_1-C_6)$-alkenyl, $(C_3-C_6)$-cycloalkyl-$(C_1-C_6)$-alkyl or $(C_1-C_6)$-alkoxy-$(C_1-C_6)$-alkyl, $R^4$ and $R^7$ are independently of one another each hydrogen or methyl, $R^3$ and $R^8$ are independently of one another each hydrogen or methyl, or $R^3$ and $R^8$ together form the group $CH_2CH_2$, $R^5$ and $R^6$ are independently of one another each hydrogen or methyl, or $R^5$ and $R^6$, together with the carbon atom to which they are attached, form the group C=O.

3. The compound and/or salt as claimed in claim 1, in which

X is chlorine or bromine,

R1 is hydrogen or methyl, $R^2$ is hydrogen, $(C_1-C_4)$-alkyl, halo-$(C_1-C_4)$-alkyl, $(C_3-C_6)$-cycloalkyl-$(C_1-C_4)$-alkyl or $(C_1-C_4)$-alkoxy-$(C_1-C_4)$-alkyl, $R^4$ and $R^7$ are independently of one another each hydrogen or methyl, $R^3$ and $R^8$ are independently of one another each hydrogen or methyl, or $R^3$ and $R^8$ together form the group $CH_2CH_2$, $R^5$ and $R^6$ are independently of one another each hydrogen or methyl, or $R^5$ and $R^6$, together with the carbon atom to which they are attached, form the group C=O.

4. A herbicidal composition which comprises a herbicidally effective amount of at least one compound and/or salt as claimed in claim 1.

5. The herbicidal composition as claimed in claim 4 in a mixture with at least one formulation auxiliary.

6. The herbicidal composition as claimed in claim 4, comprising at least one further pesticidally active compound selected from the group consisting of the insecticides, acaricides, herbicides, fungicides, safeners and growth regulators.

7. A method for controlling unwanted plants, which comprises applying an effective amount of at least one compound of the formula (I) and/or salt thereof as claimed in claim 1 to the plants and/or to the location of the unwanted plant growth.

8. A method for controlling unwanted plants comprising applying a herbicidal composition as claimed in claim 4 to the plants and/or to the location of the unwanted plant growth.

9. The method as claimed in claim 8, wherein the compound of the formula (I) and/or salt is used for controlling unwanted plants in crops of useful plants.

10. The method as claimed in claim 9, wherein the useful plants are transgenic useful plants.

* * * * *